United States Patent [19]

Neumayer et al.

[11] Patent Number: 5,675,028
[45] Date of Patent: Oct. 7, 1997

[54] BISAMIDO AZIDES OF GALLIUM, ALUMINUM AND INDIUM AND THEIR USE AS PRECURSORS FOR THE GROWTH OF NITRIDE FILMS

[75] Inventors: Deborah Ann Neumayer, Danbury, Conn.; Vikas Lakhotia, Portland, Oreg.

[73] Assignee: Board of Regents, The University of Texas System, Austin, Tex.

[21] Appl. No.: 520,680

[22] Filed: Aug. 29, 1995

[51] Int. Cl.$^6$ .............................. C07F 5/00; C04B 35/58; C01B 21/08
[52] U.S. Cl. ............................ 552/4; 556/1; 556/27; 556/176; 501/96; 501/94; 423/410
[58] Field of Search ........................... 556/1, 27, 176; 501/94, 96; 423/410; 552/4

[56] References Cited

PUBLICATIONS

Andrews and Littlejohn, "Growth of GaN Thin–Films from Triethylgallium Monamine," *J. Electrochem. Soc.*, 122(9):1273–1275, Sep., 1975.
Atwood et al., "Synthesis and Structures of [NMe$_2$(μ–NMe$_2$)GaCl]$_2$ and [TMP(μ–OEt)GaCl]$_2$ (TMP=2,6–Tetramethylpiperidide)," *J. Coord. Chem.*, 26:285–291, 1992.
Boyd et al., "Organometallic Azides as Precursors for Aluminum Nitride Thin Films," *Chemistry of Materials*, 1:119–124, 1989.
Gladfelter et al., "New Precursors for the Organometallic Chemical Vapor Deposition of Aluminum Nitride," *Mat. Res. Soc. Symp. Proc.*, 131:447–453, 1989.
Ho et al., "MOVPE of AlN and GaN by using novel precursors," *Journal of Crystal Growth*, 107:376–380, 1991.
Interrante et al., "Studies of Organometallic Precursors to Aluminum Nitride," *Mat. Res. Soc. Symp. Proc.*, 73:359–366, 1986.
Kouvetakis and Beach, "Chemical Vapor Deposition of Gallium Nitride from Diethylgallium Azide," *Chemistry of Materials*, 1:476–478, 1989.
Lakhotia et al., "GaN Film Growth Using Dimethylgalliumazide," *Materials Research Society Conference Abstract*, Boston, Massachusetts, p. 193, Dec. , 1994.
Lakhotia et al., "GaN Film Growth Using Single–Source Precursors," *Chem. Mater.*, 7(3):546–552, 1995.
Linti et al., "Darstellung und Strukteren monomerer (2,2,6,6-Tetramethylpiperidino)gallane," *Chem. Ber.*, 127:1387–1393, Mar., 1994.
Liu and Stevenson, "Growth Kinetics and Catalytic Effects in the Vapor Phase Epitaxy of Gallium Nitirde," *J. Electrochem. Soc.*, 125(7):1161–1169, Jul., 1978.
Miller and Ekerdt, "Growth of Epitaxial (100) GaAs Films Using the Single–Source Precursor [Me$_2$Ga(μ–t –Bu$_2$As)]$_2$," *Chem. Mater.*, 4:7–9, 1992.
Miller et a., "Pyrolysis Studies of the Single–Source GaAs Precursors [Me$_2$Ga(μ–As–i –Pr$_2$)]$_3$, [Me$_2$Ga(μ–AsMe$_2$)]$_3$, [Me$_2$Ga(μ–As–t –Bu$_2$)]$_2$, and [Et$_2$Ga(μ–As–t –Bu$_2$)]$_2$, " *Chem. Mater.*, 4:447–452, 1992.
Neumayer et al., "Preparation and Evaluation of Potential Single Source Compounds for Growth of Gallium Nitride Thin Films," *Materials Research Society Conference Abstracts*, Boston, Massachussetts, p. 180, Dec., 1994.
Sung et al., "Investigation of Initial Formation of Aluminum Nitride Films by Single Precursor Organometallic Chemical Vapor Deposition of [Me$_2$Al(μ–NHR)]$_2$ (R=$^i$Pr, $^t$Bu)," *Bull. Korean Chem. Soc.*, 15(1):79–83, 1994.

*Primary Examiner*—Porfirio Nazario-Gonzalez
*Attorney, Agent, or Firm*—Arnold, White & Durkee

[57] ABSTRACT

There are disclosed bisamido azides of gallium (Ga), aluminum (Al), or Indium (In) which when pyrolized in accordance with the invention, produce metal nitride films on a substrate. A representative example of a bisamido azide is bisdimethylamidogallium azide, $(CH_3)N)_2GaN_3$.

13 Claims, No Drawings

BISAMIDO AZIDES OF GALLIUM, ALUMINUM AND INDIUM AND THEIR USE AS PRECURSORS FOR THE GROWTH OF NITRIDE FILMS

The United States Government owns rights in the present invention pursuant to National Science Foundation grants CHE-8921120 and CHE-9108228.

BACKGROUND OF THE INVENTION

This invention relates to bisamido azides of the group III elements, gallium, aluminum and indium, and their use for metal organic chemical vapor deposition (MOCVD) of gallium, aluminum and indium nitrides.

Conventional growth of group III nitride films is conducted by two-source MOCVD with organometallic group III compounds such as trimethylaluminum, trimethylgallium, or trimethylindium and a nitrogen source such as ammonia, hydrazine, dimethylhydrazine or hydrazoic acid. The conventional organometallic group III MOCVD sources are pyrophoric and have stringent safety considerations for use and storage. The most commonly employed nitrogen source is ammonia. However ammonia is extremely corrosive and does not readily decompose at temperatures below 800° C. Liu et al., *J. Electrochem. Soc.*, 1978, 125:1161. Because of ammonia's high thermal stability, substrate temperatures in excess of 900° C. are routinely employed to obtain epitaxial device quality group III nitride films. The high growth temperatures introduce thermal stresses in the films and enhance impurity diffusion. Alloy formation with InN is difficult because InN can thermally dissociate at temperatures exceeding 500° C. To compensate for poor ammonia cracking efficiencies and to minimize nitrogen dissociation from the growing film, large V/III precursor ratios as great as $10^4$ (i.e., huge overpressures of ammonia) are employed. Another difficulty with ammonia is the formation of less volatile adducts with the group III alkyl precursors such as trimethylgallium, trimethylaluminum, or trimethylindium making reliable transport difficult. Alternatives to ammonia such as hydrazine ($N_2H_4$), and hydrazoic acid ($HN_3$) have been explored. However, the toxic and potentially explosive nature of the alternative nitrogen sources such as hydrazine ($TLV_{skin}$= 0.01 ppm), dimethylhydrazine and hydrazoic acid restrict their large-scale application in MOCVD.

Alternative source materials which contain both the group III and the nitrogen delivering moiety incorporated in the same molecule have been considered for the growth of group III nitrides. Polycrystalline films of GaN were grown with triethylgallium monamine $(C_2H_5)_3Ga$—$NH_3$ without an additional nitrogen source. However, triethylgallium monamine decomposed in the source bubbler to form diethylgallium amide $(C_2H_5)_2Ga$-$NH_2$, which underwent further decomposition in the source bubbler and resulted in a noticeable decrease in vapor pressure and deposition rate of GaN films. Andrews and Littlejohn, *J. Electrochem. Soc.*, 1975, 122:1273. Polycrystalline AlN growth was reported from the dimethylaluminum amide, $[(CH_3)_2AlNH_2]_3$. Sung et al., *Bull. Korean Chem. Soc.*, 1994, 15:79. However, pyrolysis of $[R_2AlNHR]_3$(R=$CH_3$, $C_2H_5$, amides with ammonia yields AlN N of improved purity and crystallinity. Interrante et al., *Mater. Res. Symp. Proc.*, 1986, p.359. Pyrolysis of similar amido compounds such as $[(CH_3)_2AlN(CH_3)_2]_2$, $[(CH_3)_2AlNCH_2CH_2]_2$, and $[(C_2H_5)_2AlNH(t$-$butyl)]_2$, which contain a nitrogen-carbon bond in the nitrogen delivering moiety resulted in large concentrations of carbon (15–38%) and oxygen (1–15%) and reduced nitrogen incorporation in the resultant AlN films. Gladfelter et al., *Mat. Res. Symp. Proc.*, 1989, 131:447. For example, AlN N films grown from $[(CH_3)_2AlN\ NH(R)]_2$, (R=i-propyl, t-butyl) were polycrystalline and contained relatively large amounts of aluminum and carbon compared to nitrogen. Sung et at., *Y. Bull. Korean Chem. Soc.*, 1994, 15:79. Polycrystalline randomly oriented AlN and GaN films have been grown with the dialkylaluminum azides $[R_2AlN\ N_3]_3$ (R=$CH_3$, $C_2H_5$) and the dialkylgallium azides $[R_2GaN_3]_3$ (R=$CH_3$, $C_2H_5$) at substrate temperatures ranging from 400°–600° C. The AlN and GaN films grown with the dialkylaluminum and gallium azides suffered from extremely high concentrations of carbon (7–22%) and oxygen (2–50%), low growth rates, poor adhesion, and nonepitaxial polycrystalline growth. Boyd et al., *Chem. Mater.*, 1989, 1:119; Ho et al., *Mat. Res. Symp. Proc.*, 1990, p.162; Ho et at., *J. Cryst. Growth*, 1991, 107:376; Kouvetakis et al., *Chem. Mater.*, 1989, 1:476.

Thus, it would be advantageous to develop safe and effective methods of producing polycrystalline metal nitride films without the associated safety concerns.

SUMMARY OF THE INVENTION

In one broad respect, the present invention is a bisamido azide of Ga, Al or In. These compounds contain labile amido leaving groups and an azide nitrogen delivering ligand for the growth of Al, Ga, and In (group III) nitride films. An important difference between these compounds and other MOCVD precursors is the combination of an azide nitrogen delivering moiety and readily cleaved amido substituents in the same molecule. More particularly, the present invention is a compound useful for metal organic chemical vapor deposition to form metals, metal nitrides and metal alloys, the compound being of formula: $[(RR'N)_2M$—$N_3]_n$ wherein R and R' are independently hydrogen, alkyl, alkyl amine, aryl, alkyl-substituted aryl, alkyl-substituted silyl, halide or together form a cycloalkyl; wherein M is Al, Ga or In; and wherein n is from 1 to about 6.

In a second broad respect, the present invention is a process for the production of a metal nitride, comprising pyrolizing at least one bisamido azide of Ga, Al, In in the presence of a substrate under conditions such that a nitride of Ga, Al, In or mixture thereof is deposited on the substrate.

The bisamido group III azides of the present invention provide one or more solutions to one or more of the aforementioned problems. For example, bisdimethylamidogallium azide (1) is not pyrophoric, does not inflame in air and is not corrosive. Growth of GaN from bisdimethylamidogallium azide does not require the addition of a nitrogen source, and only one inlet is necessary for the delivery of the compound to the growth chamber resulting in a simplified reactor design. The additional cost and safety concerns associated with handling and storing pyrophoric, potentially explosive or corrosive feedstocks is eliminated. The more facile elimination of amido ligands compared to alkyl from the gallium center in bisamido group III azides results in a significant reduction in carbon incorporation and a substantial reduction in growth temperature. For example, an amorphous GaN film with a 3.4 eV band gap was grown on (0001) sapphire with (1) at a precursor saturator temperature of 82° C. and a substrate temperature of 250° C. At a higher substrate temperature of 580° C. an epitaxial wurzitic (0001) oriented 0.7 µm GaN film with a measured band gap of 3.2 eV was deposited on (0001) sapphire in 3 hours. A non-calibrated SIMS (secondary ion mass spectroscopy) analysis of the epitaxial film grown at 580° C. revealed an oxygen content of $5\times10^{20}$ atoms/cm$^3$ and a carbon content of $2\times10^{21}$ atoms/cm$^3$.

The metal nitride films made from the bisamido metal azides of this invention are contemplated to be useful in a range of applications in the electronics industry, such as semiconductor films for use in, for instance, high-luminosity light-emitting diodes and high-speed, high-power devices that are radiation-resistant and capable of operation at high temperatures.

DETAILED DESCRIPTION OF THE INVENTION

The bisamido azides of Al, Ga or In in accordance with the above described formula, $[(RR'N)_2M\text{---}N_3]_n$, may contain a wide variety of R and R' substituents, including hydrogen, alkyl, alkyl amine, aryl, alkyl-substituted aryl, silyl, halide or together form a cycloalkyl. The alkyl groups can be linear, branched or cyclic and generally contain from 1 to 10 carbons with from 1 to 6 carbons being preferred. A representative example of a more preferred alkyl substituent is methyl. A representative example of an alkyl amine is a tertiary amine, such as ethyl(dimethyl amine). Generally, aryl contains from 6 to 20 carbon atoms with from 6 to 12 being preferred. Representative examples of such aryl groups include monoradicals of benzene, naphthalene, biphenyl and anthracene. A preferred aryl is phenyl. Generally, alkyl-substituted aryl contains from 7 to 20 carbon atoms with from 7 to about 15 being preferred with the alkyl substituents being as described above for alkyl. The alkyl-substituted aryl groups can be attached to the nitrogen via either the aromatic ring or the alkyl substituent. Representative examples of such alkyl-substituted aryl groups include monoradicals of toluene; ethylbenzene; n- and isopropylbenzene; xylene; methyl, ethyl and propyl naphthalene and polyalkylated derivatives thereof such as dimethyl naphthalene; methyl, ethyl and propyl biphenyl and polyalkylated derivatives thereof such as dimethyl biphenyl; and methyl, ethyl and propyl anthracene and polyalkylated derivatives thereof such as dimethyl anthracene. Silyl groups may be substituted with alkyl, alkyl amine, aryl alkyl-substituted aryl, or combinations thereof, with such substituents as described above. Representative examples of such alkyl-substituted silyl groups include trimethylsilyl, dimethyltertbutylsilyl, triphenylsilyl, dimethylphenylsilyl with trimethylsilyl being preferred. Preferred halides are F and Cl. When R and R' together form a cyclic alkyl group, the alkyl preferably contains 4 or 5 carbons.

Preferably, both R and R' are methyl. Preferably, M is Ga. Preferably, n is 1.

A typical compound of the present invention is synthesized by the reaction of the group III chlorides with the two equivalents of an appropriate amido lithium reagent to form the bis substituted amido metal chloride then, the bis-substituted amido metal chloride is reacted with an excess of sodium azide to form the bisamido metal azide.

The following scheme indicates synthesis and structure of three representative bisamido azides of the present invention.

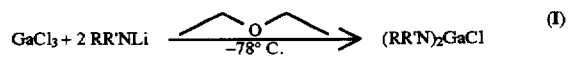

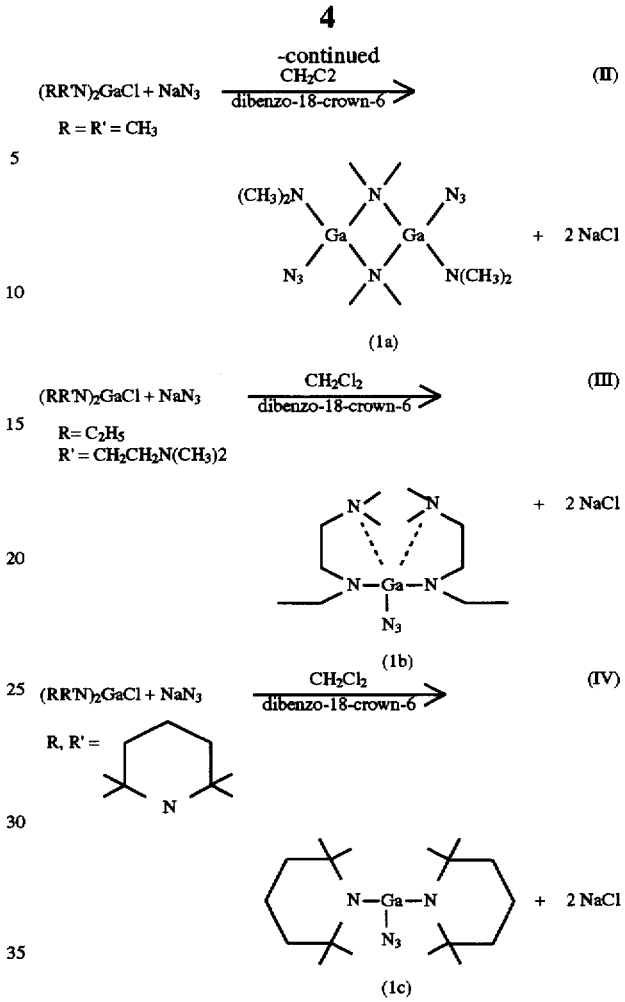

Treatment of GaCl$_3$ with two equivalents of dimethylamidolithium in ether at −78° C. afforded bisdimethylamidogallium chloride. Subsequent treatment of bisdimethylamidogallium chloride with sodium azide in dichloromethane and a catalytic mount of dibenzo-18-crown-6 afforded bisdimethylamidogallium azide (1) in high yields, following evaporation to dryness and recrystallization in pentane.

Treatment of GaCl$_3$ with two equivalents of dimethylethylethylenediamidolithium in ether results in high yields of bisdimethylethylethylenediamidogallium chloride. Subsequent treatment of bisdimethylethylethylenediamidogallium chloride with sodium azide in dichloromethane and a catalytic amount of dibenzo-18-crown-6 results in high yields of bisdimethylethylethylenediamidogallium azide (2). Complex (2) is a pale yellow liquid which is purified by distillation under reduced pressure.

Treatment of GaCl$_3$ with two equivalents of 2,2,6,6-tetramethylpiperidinolithium in ether results in high yields of bistetramethylpiperidinogallium chloride. Subsequent treatment of bistetramethylpiperidinogallium chloride with sodium azide in dichloromethane and a catalytic amount of dibenzo-18-crown-6 results in high yields of bistetramethylpiperidinogallium azide (3). Complex (3) is a pale yellow liquid which is purified by distillation under reduced pressure.

Generally, metal films are grown in the process of this invention by heating a bisamido metal azide in the presence of a substrate under conditions such that film growth occurs. Generally, the heating is conducted at an elevated temperature in the range from about 250° to about 1100° C.

The film growth process of the present invention can be carried out in metal-organic chemical vapor deposition ("CMOCVD") reactors well known to those skilled in the art, which typically ran at pressures above $10^{-2}$ Torr or a metal-organic molecular beam epitaxy reactor well known to those skilled in the art, which typically operate without carrier gases at pressures below $10^{-6}$ Torr. Another representative example of an apparatus (a system) which may be employed for epitaxial growth of nitride film is described in Miller et al., *Chem. Mater.*, 1992, 4:7, and Miller et al., *Chem. Mater.*, 1992, 4:447, which is commonly referred to as a chemical beam epitaxy system (or reactor). A reactor of this configuration is employed in Example 2, hereinafter. Generally, in such a system, a carrier gas such as hydrogen, nitrogen, argon, or helium flows into a saturator where a bisamido metal azide is located. The carrier gas flows over the bisamido metal azide and the bisamido metal azide vaporizes into the flow. Depending on the type of bisamido metal azide, the temperature of the saturator may be varied so that the bisamido metal azide vaporizes into the flow. Similarly, the flow rate of the carrier gas can be varied depending on the type of bisamido metal azide, temperature of the substrate, and so forth. Next, the bisamido metal azide-containing carrier gas flows into a heated chamber that is under reduced pressure. In the chamber, a substrate is housed on which film growth occurs. Representative examples of such substrates include sapphire, silicon and GaAs. The substrate may be cleaned prior to use. The substrate is heated to the desired temperature. Pyrolysis of the bisamido metal azide occurs in the chamber at the substrate and film growth occurs on the substrate. Generally, the chamber is maintained at subatmospheric pressures, typically $10^{-2}$ Torr or more if a MOCVD apparatus is employed or in the range of $10^{-4}$ to $10^{-5}$ Torr when a chemical beam epitaxy reactor is used. The temperature in the chamber is maintained in the range from about 250° C. to about 1100° C. with from about 400° C. to about 800° C. being preferred. It is believed that improved crystallinity is obtained at higher temperatures. In Example 2, GaAs substrate was solvent cleaned prior to use and preheated to 600° C. for about 5 minutes prior to film growth. Sapphire and quartz substrates were solvent cleaned prior to loading into the reactor.

The following examples are illustrative of the present invention and are not intended to be construed to limit the scope of the invention or claims thereof. Unless otherwise denoted, all weights and percentages are based on weight.

EXAMPLE 1

Synthesis of Bisamido Metal Azides

All manipulations were carried out under a purified argon atmosphere using standard schlenk techniques. Ether and hexane were distilled from sodium benzophenone ketyl before use. Dichloromethane was distilled from calcium hydride ($CaH_2$) before use. Sodium azide was dried in vacuo at 80° C. for 48 hours before use. Bisdimethylamidogallium chloride (Atwood et al., *J. Coord. Chem.*, 1992, 26:285) and bis-2,2,6,6-tetramethylpiperidinogallium chloride (Linti et al., *Chem. Ber.*, 1994, 127:1387) were synthesized according to published procedures.

Synthesis of bisdimethylamidogallium azide $[(Me_2N)_2GaN_3]_2(1)$. A threefold excess of sodium azide and 0.2 g of dibenzo-18-crown-6 was added to a solution of bisdimethylamidogallium chloride in dichloromethane. The reaction mixture was stirred for 24 h at room temperature. Removal of the solvent afforded a white precipitate which was extracted with pentane and filtered. The filtrate was cooled to −20° C. which afforded colorless crystals. Complex (1) is a colorless, crystalline material which may be recrystallized from hexane. In the solid state (1) is stable in air for long periods (at least 2 hours). Spectroscopic data are in accord with the structures determined by single crystal X-ray diffraction studies. mp=58°–62° C., $^1$H NMR(300.15 MHz, $C_6D_6$)δ2.30(s, broad, 6H, N—$CH_3$), $^{13}C\{^1H\}$ NMR (75.48 MHz, $C_6D_6$)42.66(s, N-$CH_3$). MS($CI^+$, isobuteine, $M=C_8H_{25}N_{10}Ga_2$): 399.075615 (399.077528).

Crystal data for (1): $C_4H_{12}N_5Ga$, M=199.91, triclinic, P$\bar{1}$, a=7.098(1), b=7.257(1), c=8.567(1)Å, α=89.57(1), β=78.74(1), γ=74.51(1)°, V=416.6(1) Å$^3$, ρ=1.594 mg/cm$^3$, Z=2, μ=32.41 mm$^{-1}$, number of reflections used=1960[$R_{(int)}$=0.0219], (2813 unique measured), R=0.0375, $R_w$=0.0472, Siemens P4 diffractomer, at −100°±1° C., graphite monochromator, Mo Kα=0.71073 Å. Atomic coordinates, bond lengths and angles, and thermal parameters have been deposited at the Cambridge Crystallographic Data Centre. The solid state structure of (1) is a polymeric chain of dimers. The dimers are bridged by the coordinative linkage of the terminal nitrogen of the azide with the gallium center of a different dimer. Each dimer features two bridging dimethylamine moieties and two terminal nonbridging azide and two terminal nonbridging dimethylamine moieties with a crystallographically imposed center of symmetry at the midpoint of the molecule. The dimer has a central $Ga_2N_2$ core which is essentially square planar. The coordination about each Ga is roughly tetrahedral.

Synthesis of bis-2,2,6,6-tetramethylpiperidinogallium azide $[(C_5H_{10}N)_2GaN_3]_2(2)$. A threefold excess of sodium azide and 0.2 g of dibenzo-18-crown-6 was added to a solution of bistetramethylpiperidinogallium chloride in dichloromethane. The reaction mixture was stirred for 24 hours at room temperature. Removal of solvent yielded a yellow liquid and colorless precipitate which was extracted with pentane and filtered. Removal of solvent from the filtrate afforded a yellow liquid which decomposed during distillation. bp 105° C. $^1$H NMR(300.15 MHz, $C_6D_6$)δ1.53 (m, 4H, $CH_2$), 1.30(s, 24H, $CH_3$), 1.23(m, 8H, $CH_2$), $^{13}C\{^1H\}$NMR (75.48 MHz, $C_6D_6$)54.2(s, NC$(CH_3)_2$), 40.2 (s, $CH_2$), 34.4(s, C$(CH_3)_2$), 18.3(s, $CH_2$). MS ($CI^+$, isobutene, $M=C_{18}H_{36}N_5Ga$): 391.221937(391.222652).

Synthesis of bisdimethylethylethylenediamidogallium azide $[(Me_2N)_2CH_2CH_2(C_2H_5)N_2GaN_3](3)$. A solution of n-butyllithium (21.3 mL, 0.0341 mole, 1.6M hexane solution) was added to a stirring solution of dimethylethylethylenediamine (3.96 g, 0.0341 mole) in ether at −78° C. The reaction mixture was allowed to warm to 25° C. and stirred for 2 hours. The dimethylethylethylenediamidolithium solution was added dropwise to a stirred solution of $GaCl_3$ in ether at −78° C. The reaction mixture was allowed to warm to 25° C. and stirred overnight. Removal of the solvent afforded a white precipitate which was extracted with pentane and filtered. Removal of solvent yielded the bisdimethylethylethylenediamidogallium chloride which was used without further purification. A threefold excess of sodium azide was added to a solution of bisdimethylethylethylenediamidogallium chloride in benzene. The reaction mixture was stirred for 24 hours at room temperature. Removal of the solvent afforded a white precipitate which was extracted with pentane and filtered. Removal of solvent yielded a yellow liquid which was purified by distillation under reduced pressure. bp=95° C./$10^{-2}$ Torr, $^1$H NMR (300.15 MHz, $C_6D_6$)δ2.67(t, 2H, N-$CH_2$), 2.59(q, 2H, N$CH_2CH_3$), 2.38(t, 2H, N-$CH_2$), 2.14(s, 6H, N-$CH_3$), 0.98 (s, 3H, $CH_2CH_3$), $^{13}C\{^1H\}$NMR(75.48 MHz, $C_6D_6$)58.56

(s, N-CH$_3$), 50.08(s, N—CH$_2$)46.39(s, N—CH$_2$)46.00 (s, N—CH$_2$), 12.38(s, CH$_2$CH$_3$). MS (CI$^+$, isobutene, M=C$_8$H$_{25}$N$_{10}$Ga$_2$): 341.181058(341.181850).

Example 1 demonstrates preparation of representative examples fothe bisamide metal azides of the present invention.

EXAMPLE 2

Metal Nitride Film Growth

Film growth experiments were carried out in a stainless steel chemical beam epitaxy reactor in the temperature range 250°–620° C. Bisdimethylamidogallium azide (1) was placed in a stainless saturator and heated in an oven to 82° C. Lines downstream of the saturator were heated by the oven or by heating tapes to prevent recondensation of the sublimed precursor. During growth, a helium carrier gas was used to transport the precursor to the substrate surface. The substrate is glued with indium onto a tantalum foil and placed on a tantalum stage and resistively heated. In agreement with the thermolysis results, it was found that GaN film growth (on (0001) sapphire) with bisdimethylamidogallium azide could be achieved as low as 250° C. Despite the amorphous nature of these films, they exhibited the correct band gap for GaN (3.4 eV). Epitaxial growth of GaN on (0001) sapphire was achieved by employing higher deposition temperatures. The θ–2θ X-ray diffraction (XRD) scan of GaN deposited at 460° C. revealed the persistence of slight polycrystallinity. However, by 580° C. these additional features had disappeared leaving only the peaks at 2θ of 34.6° and 73° which could correspond to either the wurzitic ((0002) and (0004) planes, respectively) or the cubic ((111) or (222) planes, respectively) phases of GaN. This question was resolved by means of a χscan which revealed that the phase is wurzitic. Further confirmation of epitaxial crystalline growth was provided by pole figure analysis of a 0.7 μm thick film. The full width at half maximum of the 2θ peak at 34.6° was ~12 arcmin$^{-1}$.

When the substrate was changed to (100) GaAs, polycrystalline growth was observed at 500° C. as evidenced by the appearance of XRD peaks at 34.6° ((111) or (0002) plane) and 40.1° ((002) plane). Ramping the deposition temperature to 620° C. (the limit of GaAs stability) resulted in an increase of intensity of the 40.1° peak at the expense of the 34.6° peak thus suggesting the approach to epitaxial growth to cubic GaN. SEM examination of GaN film growth on (0001) sapphire at 580° C. indicated a smooth, crack free morphology with an absence of surface features up to a magnification of 48,000×. The stoichiometric nature of the films was confirmed by X-ray photoelectron spectroscopy. Using GaAs implanted standards, a non calibrated SIMS (secondary ion mass spectroscopy) analysis of the epitaxial film grown at 580° C. resulted in estimated oxygen and carbon contents of 5×10$^{20}$ atoms/cm$^3$ and 2×10$^{21}$ atoms/cm$^3$, respectively.

Example 2 demonstrates production on metal nitride film using the single-source bisamido metal azides of the present invention.

What is claimed is:

1. A bisamido azide of Ga, Al or In.

2. The azide according to claim 1, wherein the azide is of Ga.

3. The azide according to claim 1, wherein the azide is of Al.

4. The azide according to claim 1, wherein the azide is of In.

5. The bisamido azide of the formula [(RR'N)$_2$M—N$_3$]$_n$ wherein R and R' are independently hydrogen, alkyl, alkyl amine, aryl, alkyl-substituted aryl, alkyl-substituted silyl, halide or together form a cycloalkyl;

wherein M is Ga, Al or In; and wherein n is from 1 to about 6.

6. The azide according to claim 5, wherein R and R' are alkyl of from 1 to 4 carbons.

7. The azide according to claim 6, wherein R and R' are methyl.

8. The azide according to claim 5, wherein M is Ga.

9. The azide according to claim 5, wherein M is Al.

10. The azide according to claim 5, wherein M is In.

11. The azide according to claim 6, wherein M is Ga and n is 1.

12. The azide of claim 5, wherein R and R' together form a cycloalkyl.

13. The azide of claim 5, wherein R is alkyl amine and R' is alkyl of 1 to 4 carbons.

* * * * *

UNITED STATES PATENT AND TRADEMARK OFFICE
CERTIFICATE OF CORRECTION

PATENT NO. : 5,675,028

DATED : October 7, 1997

INVENTOR(S) : Deborah Ann Neumayer and Vikas Lakhotia

It is certified that error appears in the above-identified patent and that said Letters Patent is hereby corrected as shown below:

In claim 5, column 8, line 28, delete "Ca" and insert --Ga-- therefor.

Signed and Sealed this

Twenty-third Day of December, 1997

Attest:

BRUCE LEHMAN

Attesting Officer

Commissioner of Patents and Trademarks